(12) United States Patent
Haq et al.

(10) Patent No.: US 6,492,460 B2
(45) Date of Patent: Dec. 10, 2002

(54) LINKER BASED SOLID SUPPORT FOR PEPTIDE AND SMALL MOLECULE ORGANIC SYNTHESIS

(75) Inventors: Wahajul Haq; Seturam Bandhacharya Katti, both of Uttar Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/771,108

(22) Filed: Jan. 26, 2001

(65) Prior Publication Data

US 2002/0147297 A1 Oct. 10, 2002

(51) Int. Cl.$^7$ ................................................ C08G 63/48
(52) U.S. Cl. ........................................ 525/50; 525/54.1
(58) Field of Search ................................... 525/50, 54.1

(56) References Cited

U.S. PATENT DOCUMENTS

| 3,743,628 A | | 7/1973 | Bodanszky et al. | 530/334 |
| 4,764,594 A | * | 8/1988 | Getman | 530/334 |

FOREIGN PATENT DOCUMENTS

| EP | 0 273 895 | 7/1988 |

* cited by examiner

*Primary Examiner*—Terressa M. Boykin
(74) *Attorney, Agent, or Firm*—Ladas & Parry

(57) ABSTRACT

The present invention relates to a novel linker based solid support, methods for generating the linker moiety on the solid support, and methods of using the supports to synthesize peptides and small molecule combinatorial library and the new solid support of this invention also comprises a functionalized linker covalently attached to the solid supports such as polystyrene.

25 Claims, 7 Drawing Sheets

Hydroxyethyl-sulphenyl-acetamido-resin (1)

Hydroxyethyl-sulphenyl-acetamido-resin (1)

R= H, Cl, Br, I, F, $NO_2$, OH, OMe, alky, aralkyl, aryl and substituted ones
X= C or N
R'= Acyl, alkyl, Boc, Bz, Z or aminoacids
R"= Amino protecting group Synthesis of thiazolidine derivatives R= H, Cl, Br, I, F, NO$_2$, OH, OMe, alky, aralkyl, aryl and substituted ones
X= C or N
R'= Acyl, alkyl, Boc, Bz, Z or aminoacids
R"= Amino protecting group

LINKER BASED SOLID SUPPORT FOR PEPTIDE AND SMALL MOLECULE ORGANIC SYNTHESIS

FIELD OF THE INVENTION

The present invention relates to a novel linker based solid support for use in peptide synthesis and combinatorial library synthesis, methods for generating the linker moiety on the solid support, and methods of using the supports to synthesize peptides and small molecule combinatorial libraries. The new solid support of this invention also comprises a functionalized linker covalently attached to the solid supports such as polystyrene.

BACKGROUND INFORMATION

Rapid development of solid phase synthesis calls for the development of new and versatile solid support to meet the newer synthetic challenges. The solid supports for the synthesis of peptides have been very well established and even synthesis of cyclic peptides, peptide amides, peptide aldehydes etc are now possible directly on the support [(a) Barany, G. et al., *Int. J. Peptide protein Res.* 30, 705–739, 1987.; (b) Fields, G. B. et al., *Int. J. Peptide protein Res.* 35, 161–214, 1990. (c) Lloyd-Williams, P. et al., *Tetrahedron*, 49, 11065–11133, 1993 (d) Wang, S. S., *J. Amer. Chem. Soc.* 95, 1328, 1973 (e) Barlos, K., et al., *Tetrahedron Letters*, 30, 3947, 1989 (f) Beebe, X., et al., *J. Org. Chem.*, 60, 4204, 1995 (g) Rink, H., *Tetrahedron Letters*, 28, 3787, 1987 (h) Rapp, W., et al., in "*Peptides 1988*", *Proc. 20th European Peptide Symposium*, Jung G. and Boyer E. (Eds.), Walker de Gruyter, Berlin, pp 199 1989]. Further, synthesis of small organic molecules require more versatile and broad range solid supports. A number of supports are reported in the literature with a variety of functionalities to attach the synthons as well as their stability and susceptibility towards the synthetic reagents and experimental conditions used [Oesapay, G., et al, in "*Peptides Chemistry, Structure and Biology, Proc. 13th American Peptide Symposium*", Hodges, R. S. and Smith J. A. (Eds.), *ESCOM, Leiden*, pp 435, 1994, (b) Hermkens, P. H. H. et al, *Tetrahedron*, 52, 4527, 1996 (c) Hermkens, P. H. H. et al, *Tetrahedron*, 53, 5643, 1997 (d) Brown, R. C., *J. Chem. Soc. Perkin-I*, 3293, 1998]. Mostly, the available supports require drastic conditions for the cleavage of molecules from the solid support involving strong acids, which are harmful to the molecules. Further, aminolysis and reductive cleavage methods result in side reaction and racemization, particularly in the case of peptides. On the other hand, supports, which require relatively milder conditions, do not withstand various reagents and experimental conditions used in organic synthesis, particularly in the case of small organic molecules. Therefore, development of new and versatile supports, which are orthogonal compatible, will be highly beneficial.

Development of various supports essentially based on the strategy to incorporate a bi-functional linker between the solid matrix and growing molecule are in vogue. The first step involves attachment of linker molecule on the solid matrix and subsequently the desired synthetic scaffold is constructed on the linker bearing solid support. This allows utilization of the desired functionalities for the attachment of synthetic scaffold and to achieve desired chemical properties on the solid support. Based on this premise a number of linker based solid supports have been developed and are in commercial use [Oesapay, G., et al, in "*Peptides Chemistry, Structure and Biology, Proc. 13th American Peptide Symposium*", Hodges, R. S. and Smith J. A. (Eds.), *ESCOM, Leiden*, pp 435, 1994, (b) Hermkens, P. H. H. et al, *Tetrahedron*, 52, 4527, 1996 (c) Hermkens, P. H. H. et al, *Tetrahedron*, 53, 5643, 1997 (d) Brown, R. C., *J. Chem. Soc. Perkin-I*, 3293, 1998. And a) Blackburn, C. *Biopolymers, peptide sciences*, 47, 311, 1998 (b) Patek, M. and Lebl, M. ibid. 353 (c) Barany, G., et al, U.S. Pat. No.:5,235,028 1993.(d) Barany, G., U.S. Pat. No.:5,306,562, 1994 (e) Jensen, K. J., et al., U.S. Pat. No. 5,917,015, 1999].

Working on similar lines, the applicants also developed earlier a linker for solid phase synthesis of peptides [Katti, S. B. et al, *J. Chem. Soc. Chem. Commun.*, 843–844, 1992]. The base labile linker as shown in FIG. II, formula VII was prepared using readily available raw materials and synthesized for each amino acid separately to be used at C-terminal. It was prepared according to the method used for the synthesis of PAM resin [Mitchell, A. R. et al., *J. Org. Chem.* 43, 2845, 1978]. This provides pre-loaded amino acid with linker on solid support for further synthesis of peptides. The synthesis started with the treatment of chloroacetic acid (I) with phenacyl bromide (II) to obtain corresponding ester (III). The ester III was treated with mercaptoethanol (IV) to obtain protected linker (V). The hydroxy group of the linker was acylated with suitably protected amino acid (Boc or Fmoc) with DCC and DMAP followed by the deblocking of phenacyl ester by Zn/AcOH to obtain free acid (VI). The sulfide group of the free acid VI was then oxidized to obtain corresponding sulphone (VII) by the treatment with oxone. The linker acid carrying the suitably protected amino acid was loaded on the amino methyl resin by DIC/HOBT procedure and quantitative loading was obtained. Having loaded the linker bearing first amino acid on solid support, the utility of linker based solid support was demonstrated by synthesis of peptides using Boc and Fmoc chemistry employing the known procedures. The cleavage of the peptide from the solid support was carried out under extremely mild conditions by treatment with dioxane:methanol:4N NaOH (30:9:1) for 30 min. This provides an opportunity to obtain protected peptide fragments, which are quite useful intermediates for the synthesis of large peptides and proteins [Kaiser, E. T., *Acc. Chem. Res.* 22, 47, 1989; Williams, P. et al. *Tetrahedron*, 49, 11065, 1993]. Thus, it was demonstrated that the linker was compatible with both, Boc and Fmoc chemistry protocols and can be synthesized easily in laboratory. Using this linker several peptides and protected peptide fragments have been synthesized.

Technical Problem

In spite of the various advantages, there are certain limitations with the linker based solid support mentioned above. For the synthesis of peptides the linker with the amino acid at the C-terminus is to be synthesized separately for each synthesis [FIG. II shown in the accompanying drawings]. Therefore, the synthesis for each sequence requires additional steps and longer time. Further, the linker having protected amino acid is oxidized using oxone, a powerful oxidizing agent, before loading it on the solid support, therefore, amino acids, prone to oxidation can not be used as the first amino acid. Thus peptide sequences having cystein, methionine, tryptophan and tyrosine at the C-terminus pose problems as these amino acids are oxidized during the oxone oxidation. Secondly, it has been observed that the linker of formula VII, as shown in FIG. II of the accompanying drawings is not completely stable under the cleavage conditions used for the removal of Fmoc group, particularly for the synthesis of longer peptides. It was observed that prolonged exposure with 20% piperidine solution resulted in the cleavage of growing chain from the solid support. Since the cleavage of products from the solid support occurs via β-elimination, the basicity of the 20% piperidine solution is enough to cause the β-elimination of the linker and resulted in the partial cleavage of the peptide at each deblocking step.

OBJECTIVES OF THE INVENTION

The main objective of the present invention is to provide an orthogonally compatible linker based solid support for organic synthesis.

Another objective of the invention is to provide a new linker based solid support for peptide synthesis employing Boc and Fmoc chemistry protocols separately or in combination.

One more objective of the invention is to provide a new solid support comprising a functionalized linker covalently attached to the solid supports such as polystyrene.

Another objective of the present invention is to provide a method of synthesis of hydroxyethyl-sulphenyl-acetamido resin.

Still another objective of the invention is to provide a new solid support for the synthesis of protected peptide fragments for use in solid phase convergent synthesis of longer peptides.

Yet, another objective of the present invention is to enhance the scope of the new linker based solid support for the synthesis of small organic molecules to generate combinatorial libraries

BRIEF DESCRIPTION OF THE ACCOMPANYING DRAWINGS

In the accompanying drawings.

SUMMARY OF THE INVENTION

Figure 1:
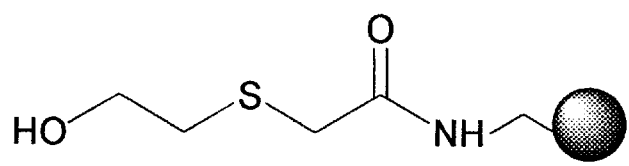
FIG. 1 show the structure of hydroxyethyl-sulphenyl-acetamido resin
Figure 2:
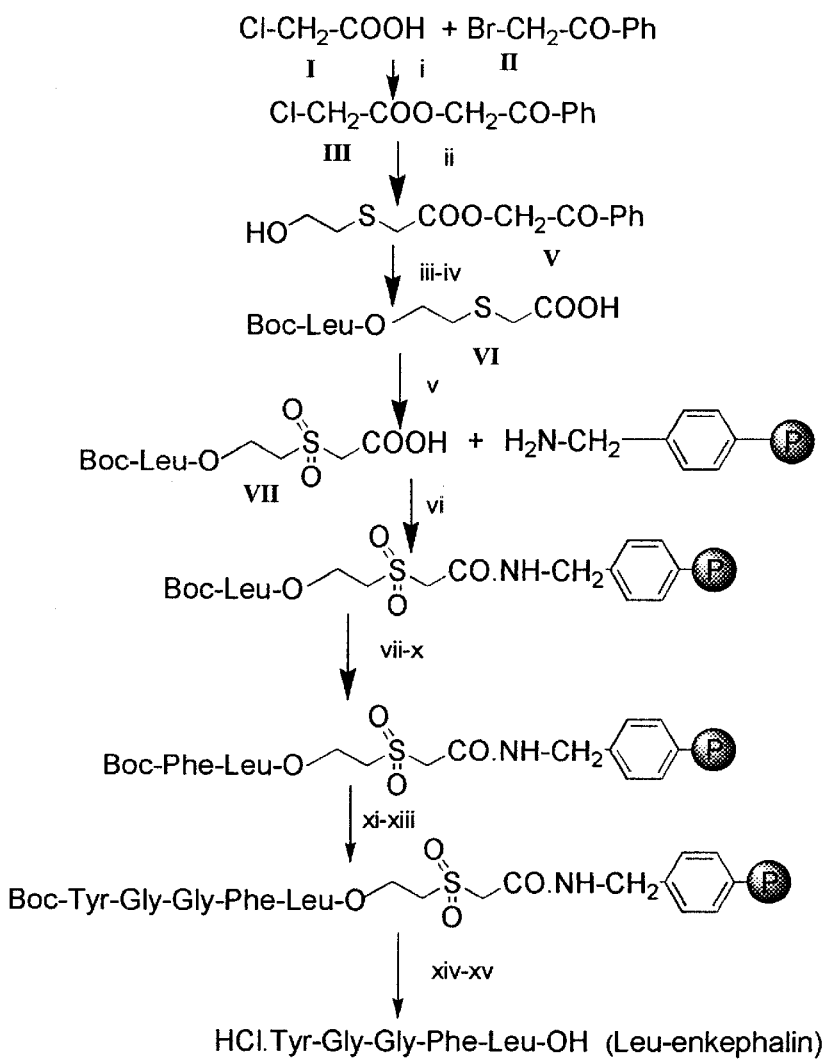
FIG. 2 represents the conventional synthesis of pepdites
Figure 3:
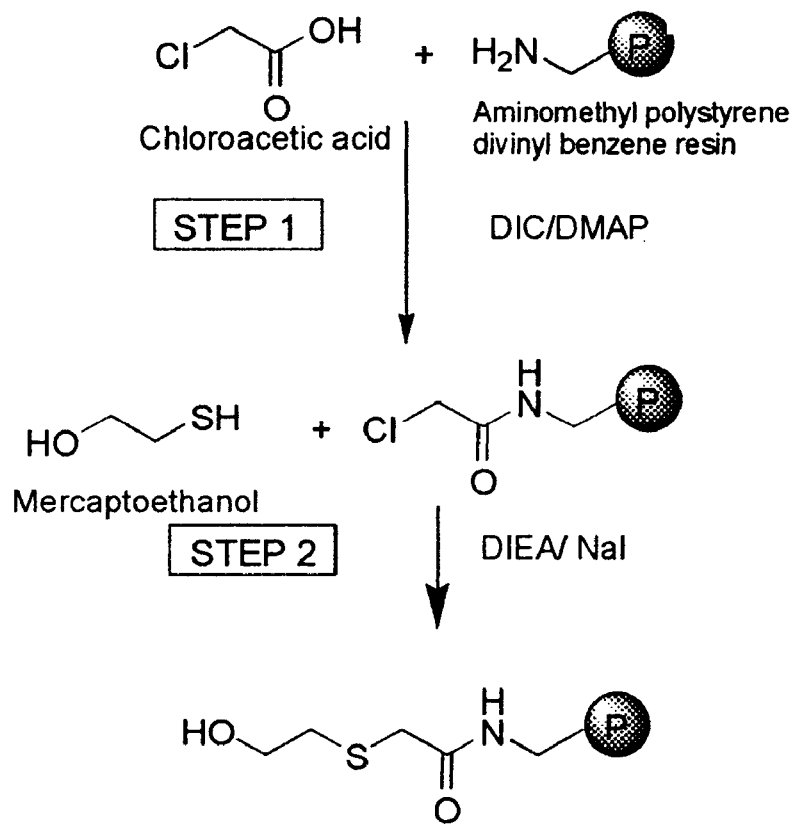
FIG. 3 represents the synthesis of hydroxyethyl-sulphenyl-acetamido resin (HESA)
Figure 4:
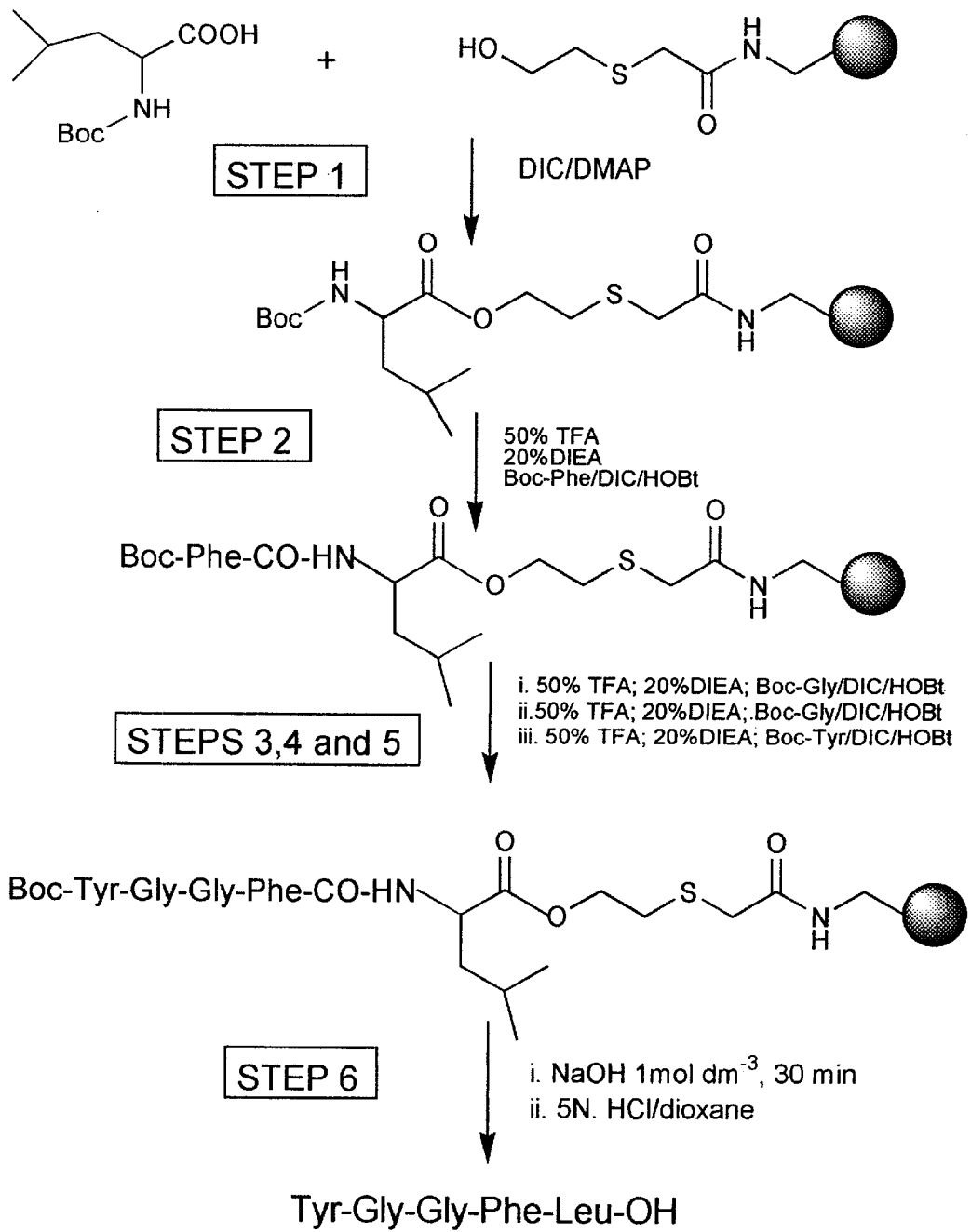
FIG. 4 represents the synthesis of Tyr-Gly-Gly-Phe-Leu-OH by Boc chemistry protocol.
Figure 5:
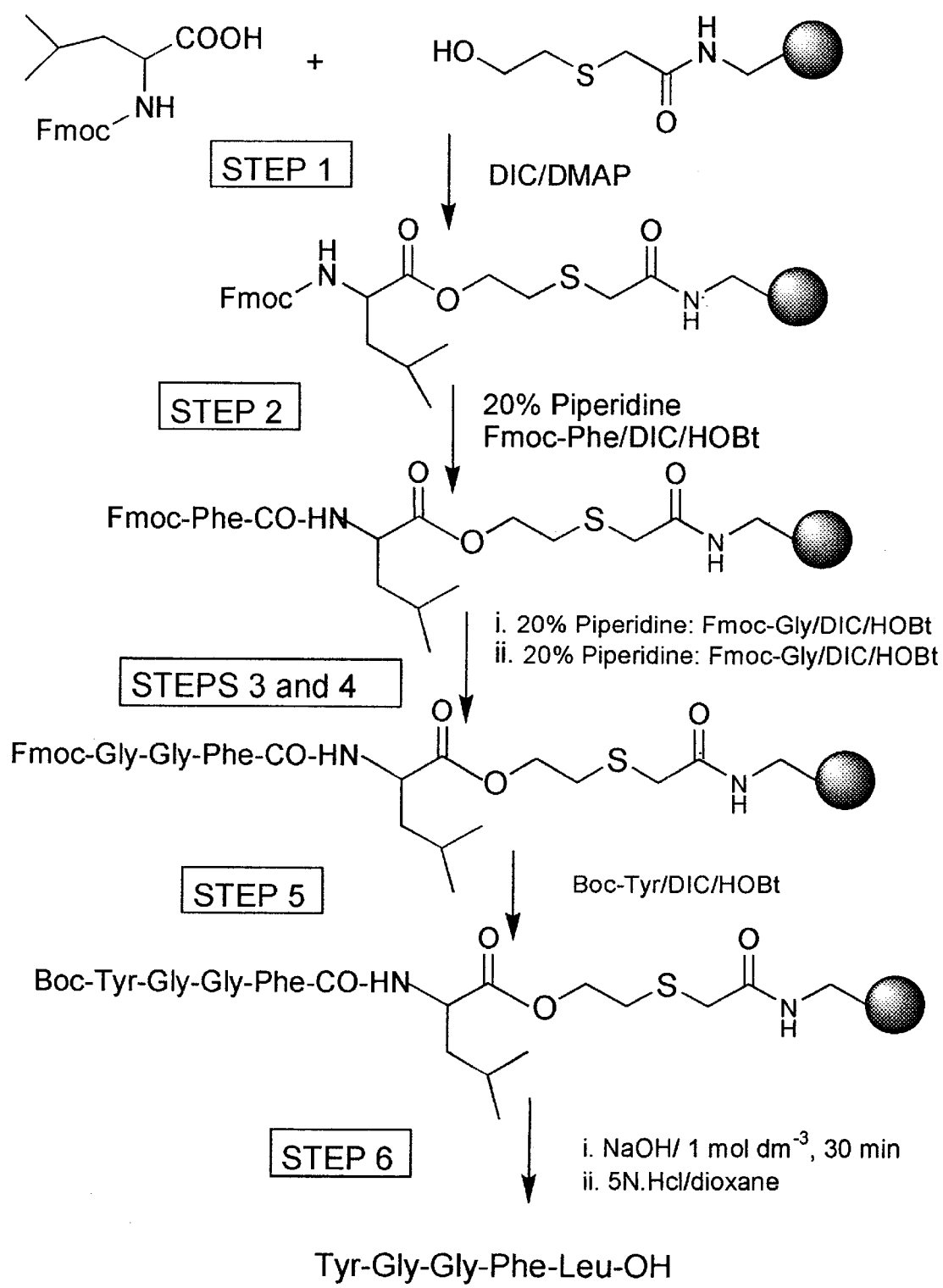
FIG. 5 represents the synthesis of Tyr-Gly-Gly-Phe-Leu-OH by Fmoc chemistry protocol
Figure 6:
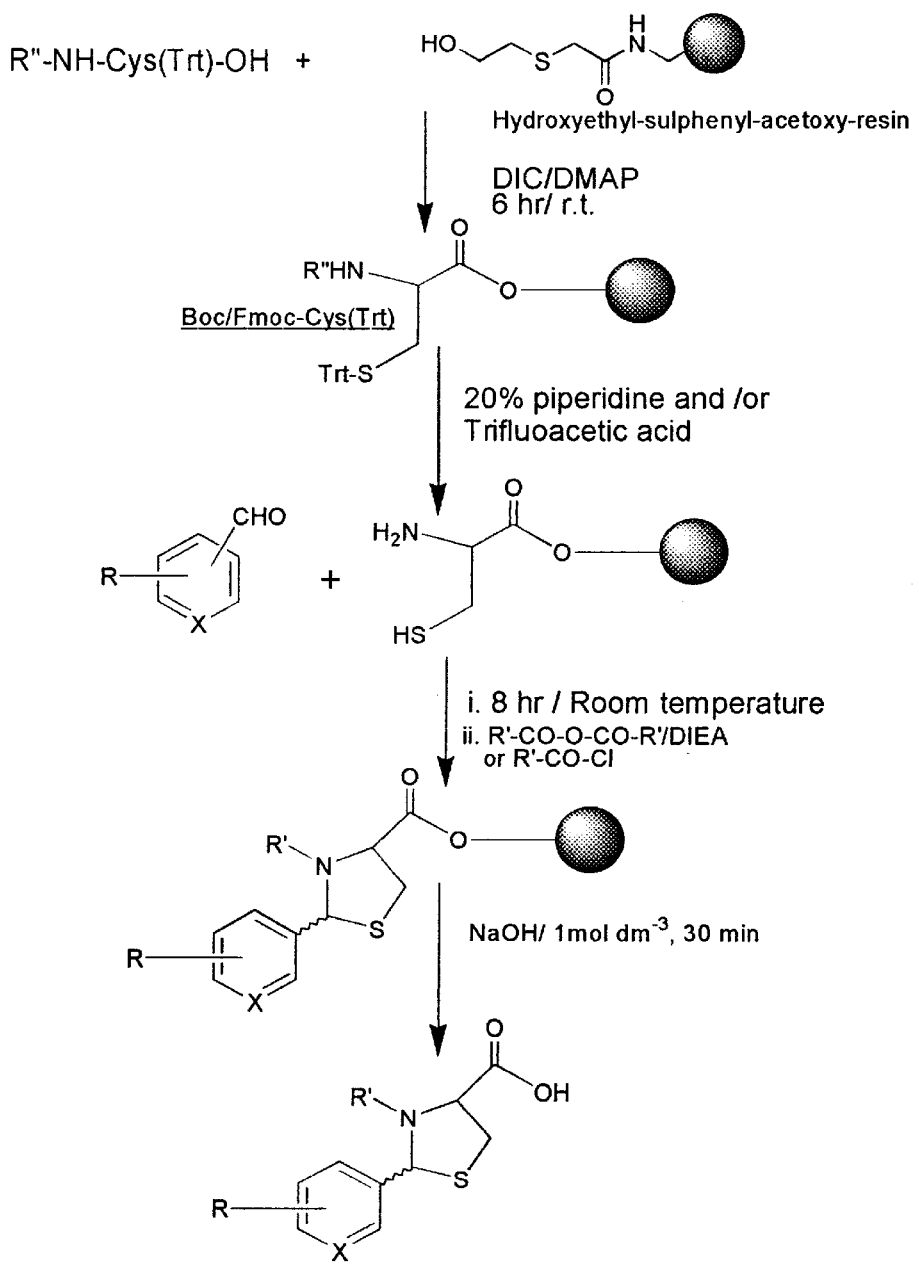
FIGS. 6 and 7 represent synthesis of thiazolidine derivatives.
Figure 7:
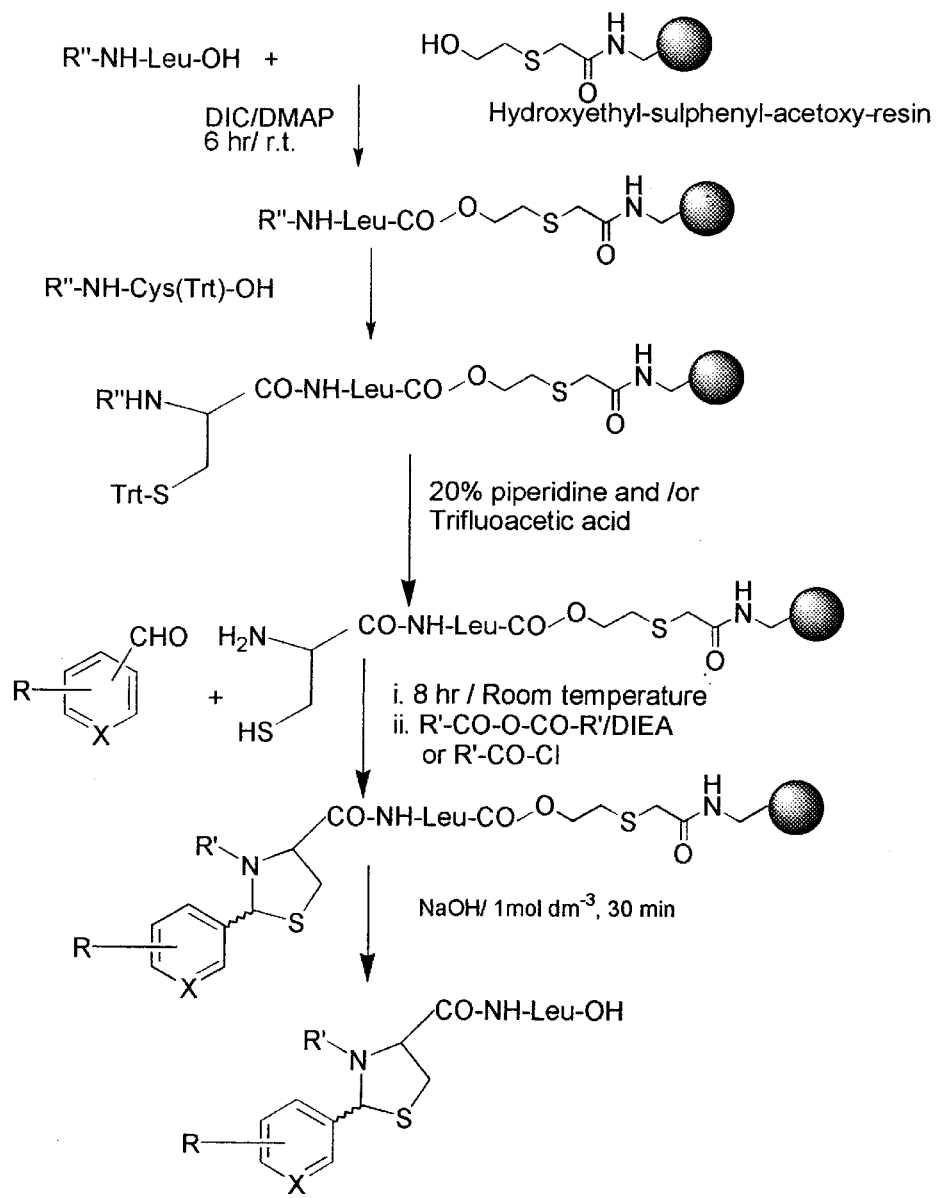

To meet the above objectives, the present invention describes the development of a new orthogonally compatible solid support, hydroxyethyl-sulphenyl-acetamido resin (HESA resin) as shown in formula 1 FIG. I. The new solid support described herein can be used for the synthesis of biologically active peptides using both Boc and Fmoc chemistry separately or in combination.

DETAILED DESCRIPTION OF THE INVENTION

The field of solid phase synthesis and combinatorial chemistry have coalesced and emerged as useful tools for new leads discovery. Fueled largely by the drug industry and its quest for more compounds, solid phase synthesis has been adopted to many organic transformations. In concert with this renewed interest is an opportunity for technology development namely new linkers and/or solid support tailored to handle the demands of organic synthesis. The available solid supports with diverse chemical properties, although, conceptually elegant, are suitable for one or the other type of chemistry and involve sophisticated chemistry. The present support is easily accessible from commercially available and cheap raw materials. The final products can be cleaved under very mild conditions. The present invention describes the synthesis and application of a new linker based solid support for the synthesis of peptides and small molecules for generation of combinatorial libraries.

Since it requires a very mild basic condition for the cleavage of the products from the support, it offers rapid synthesis of protected peptides fragments, which are useful for the convergent synthesis of large peptides. The peptides synthesized are of high yield and excellent purity. Further the products are free from racemization. This also allows synthesis of sequences with oxidation prone amino acids at the C-terminus. Another important feature of the invention that the new solid support can be used for the solid phase synthesis of small organic molecules and generation of combinatorial libraries of peptides and small organic as well as heterocyclic molecules. The new solid support can be synthesized very conveniently in the laboratory in bulk and does not require any special precaution during storage and can be stored for months at ambient temperature for subsequent synthetic applications. Further, a new and novel method has also been developed for its synthesis.

The synthesis of new solid support with a chemically defined reactive handle was accomplished in two steps. In the first step chloroacetic acid or its equivalent containing a suitable leaving in place of halogen is coupled with amino methyl resin by the known procedure [STEP-1] as shown in FIG. III of the accompanying drawings. This reaction step is quantitative as indicated by the negative Kaiser test. In the next step mercaptoethanol was reacted with the solid support, obtained from, step 1 to get the desired solid support 1 [STEP-2] as shown in FIG. III of the accompanying drawings. The new linker based solid support 1 as shown in the accompanying drawings was characterized on the basis of a strong peak at 1666 cm$^{-1}$ corresponding to the carbonyl of the newly introduced acetamido moiety and a peak at 3219 cm$^{-1}$ corresponding to the primary hydroxy group.

The quantitation of the hydroxy functional group was carried out by the standard procedures reported in the literature by loading the appropriate Boc or Fmoc protected amino acids employing standard protocol. In case of Boc-chemistry, the quantitation was carried out by estimation of the amino functional group on the solid support by picric acid method [Method A] [Gisin, B. F., *Anal. Chim. Acta.*, 58, 248, 1972]. Whereas in the case of Fmoc chemistry, the Fmoc group was removed by the piperidine treatment and subsequently the 9-fluorenylmethyl piperidine was quantitated by measuring the absorbance at 301 nm [Method B] [Meienhofer, J. et al., *Int. J. Peptide protein Res.* 13, 35, 1979]. The new resin 1, was found to be stable at ambient temperature for several months and once prepared, can be used for a long time for the subsequent synthetic applications without any special storage conditions. Further, the resin bearing amino acid was also tested for stability towards the reagents and experimental conditions commonly used for peptide synthesis during Boc and Fmoc chemistry protocols. The applicants did not observe any cleavage of the resin bound amino acid under 50% TFA:DCM as well as 20% piperidine in DMF.

Racemization Studies:

Although the alkaline conditions for the cleavage of peptide from the resin are quite mild, the applicants thought it appropriate to provide some definite evidence about the risk of racemization. A pair of protected dipeptide, Boc-Gly-L-Phe-OH and Boc-Gly-D-Phe-OH was synthesized for this purpose. This dipeptide was chosen because the enzyme carboxypeptidase-A preferentially hydrolyses the peptide bond next to an aromatic amino acid at the C-terminal [Bradshaw, R. A., et al. Proc. Natl. Acad. Sci. U.S.A., 63, 1389, 1969]. During peptide cleavage from the support if the racemization were to occur we should expect a peak corresponding to unhydrolysed dipeptide in the case of Boc-Gly-L-Phe-OH, while there should be some hydrolysis in the case of Boc-Gly-D-Phe-OH depending on the extent of racemization. The protected dipeptides after removal from the solid support without further purification were subjected to enzymatic hydrolysis by carboxypeptidase-A. After 30 min aliquots were monitored by TLC. Boc-Gly-L-Phe-OH was completely hydrolyzed and in its place two spots corresponding to Boc-Gly and L-Phenylalanine were observed. While Boc-Gly-D-Phe-OH was completely resistant to hydrolysis as seen by the absence of spots corresponding to the hydrolytic products and the dipeptide was intact. The monitoring was also performed by HPLC and similar results were obtained. Complete hydrolysis was observed in the case of Boc-Gly-L-Phe-OH, whereas no hydrolytic cleavage was observed in the case of Boc-Gly-D-Phe-OH as evident by the absence of peak corresponding to Boc-Gly in the HPLC profile. These results unequivocally demonstrate that there is no racemization of the C-terminal amino acid during the removal of the peptide from the solid support.

Synthetic Applications of the Linker Based Solid Support:

To demonstrate the utility of this linker, synthesis of some peptides using Boc and Fmoc chemistry and several thiazolidine derivatives has been carried out. Leu-enkephalin has been synthesized by Boc-chemistry and Fmoc chemistry separately. A stepwise deprotection/coupling cycle to incorporate subsequent amino acid residues was accomplished by the standard DIC/HOBt protocol. Deblocking of Boc group was carried out by 50% TFA in DCM or 5N HCl/dioxane and Fmoc group by 20% piperidine/DMF. At each step coupling reactions were repeated, if so required as judged by the Kaiser test, to achieve better yields. The final peptides were detached from the solid support under alkaline conditions and treated with 5N.HCl/dioxane. After work-up and crystallization, all peptides were obtained in more than 60–70% overall yield. They have been characterized by spectroscopic methods.

All the compounds were found to be more than 90% pure in reversed phase HPLC and gave correct molecular ion peaks in FAB-MS. In order to expand the scope of the present linker, it was thought desirable to synthesize peptides having side chain functionalities. A pentapeptide, Lys-Thr-Thr-Lys-Ser, corresponding to residues 211–216 of the type-I pro-collagen was chosen for this purpose [Katayama K. et al, J. Biol. Chem., 268, 9941, 1993]. Synthesis was carried out by Boc chemistry using DIC/HOBT for coupling reactions. Boc-Ser(Bzl) was attached to the linker following the same protocol as shown in FIG. IV. This was followed by sequential addition of suitably protected amino acids. At the end of the synthesis the amino and side chain protected peptide was cleaved from the solid support as described earlier. The protected peptide fragment was characterized by the molecular ion peak at appropriate [M+H]$^+$ in the FAB-MS spectrum. The fact that the peptide can be selectively cleaved from the solid support keeping amino and side chain protecting groups intact suggests that this linker could be useful in synthesis of larger peptides by fragment condensation method. Finally, the protecting groups were removed quantitatively and the pentapeptide was obtained in 78% yield.

To demonstrate the application of novel solid support in the synthesis of small organic molecule, several thiazolidine derivatives [Patek, M., et al, Tetrahedron Letters 36, 2227, 1995] have been synthesized. The protocol adapted for the synthesis is shown in the scheme (FIGS. VI and VII). Appropriately protected cystein derivative viz. Fmoc-Cys (Trt) was attached to the solid support by DIC/DMAP or any other catalyst using the protocol described for the synthesis of peptides. The Fmoc group was cleaved by the treatment with 20% piperidine in DMF and subsequently trityl group was removed by the treatment with 10% TFA in DCM. The support bound cystein having free amino and sulphhydryl groups was reacted with desired commercially available aldehydes (using 2 molar excess) at room temperature or at elevated temperature. The cyclization was complete in 6–8 hrs. Alternatively, the thiazolidine(s) was also successfully synthesized using Boc-Cys (trt) as starting material bound to the solid support. The advantage of this derivative is that the protecting groups from the amino and sulphydryl groups can be removed in a single step i.e. TFA treatment. The thiazolidine derivative thus, obtained can be cleaved from the solid support as such or could be derivatized/acylated on the solid support. Thus, the support bearing a thiazolidine was divided into several portions and the free amino function was acylated separately with different aromatic and aliphatic acylating agents in parallel synthesis protocol. Using various aldehydes and acylating agents a number new derivatives were generated in high yields and purity.

In order to enhance, the scope of the linker based solid support as shown in FIG. I formula 1 as shown in the accompanying drawings, the thiazolidine skeleton was synthesized on different amino acids/peptides or any other molecule bound to the support. Thus, a suitably protected Boc or Fmoc protected amino acid was attached to the solid support using standard protocol. The amino protecting group was removed and the free amine was coupled with appropriately protected cystein residue by DIC/HOBt method. After complete coupling, as monitored by Kaiser test, both the protecting groups of cystein were removed in the same manner as described earlier. The resin bearing the dipeptide with free amino and sulphydryl groups of cystein was allowed to react with desired commercially available aldehydes (using 2 molar excess) on solid support at room temperature. The cyclization was complete in 6–8 hrs. The thiazolidinyl dipeptide derivative(s) thus, obtained can be cleaved from the solid support as such or could be derivatized/acylated on the solid support. The support bearing a thiazolidinyl dipeptide derivative(s) was divided into several portions and the free amino function was acylated separately with different aromatic and aliphatic acylating agents in parallel synthesis protocol. Using various C-terminal amino acids, different aldehydes and acylating agents a vide variety of new compounds were generated in high yields and purity.

In short, the new linker can be conveniently synthesized in the laboratory and it is ideally suited for peptide synthesis by the Boc and Fmoc chemistry protocols. Protected peptides can be synthesized for use in segment condensation method. The conditions employed in the detachment of the peptide from the solid support do not lead to racemization. We believe that the new linker reported here is stable to acidic and mild basic conditions, hence it has tremendous potential for use in peptide/oligonucleotide synthesis and a wide variety of small molecule library construction.

Accordingly, the present invention relates to development of hydroxyethyl-sulphenyl-acetamido-Resin, an orthogonally compatible solid support for the solid phase synthesis of peptides and protected peptide fragments using Boc and Fmoc chemistry separately or in combination as well as for the synthesis of small organic molecule combinatorial libraries. The present invention also provides a novel process for the synthesis of hydroxyethyl-sulphenyl-acetamido-Resin having the formula as shown in formula 1, of FIG. I, wherein, the solid support is selected from the group consisting of amino functional membranes, porous glass, polystyrene, cotton and paper and the polystyrene is selected from the group consisting of aminopolystyrene and aminomethyl polystyrene, said process comprises;

(a) reacting chloroacetic acid, or its equivalent containing a suitable leaving group in place of halogen, with amino methyl resin in the presence of diisopropylcarbidiimide or any other commonly used coupling reagent using the known procedures [sequence as shown in FIG. III of the accompanying drawings].

(b) reacting above solid support having a leaving group with mercaptoethanol in presence of sodium iodide to get the desired solid support of the formula 1, FIG. III and if desired, (c) the novel solid support thus obtained is utilized for the synthesis of peptides, protected peptide fragments and small organic molecules as shown in FIGS. IV–VII of the accompanying drawings.

According to the further feature of the invention, the synthesis of the linker based solid support was carried out using easily accessible and commercially available cheap raw materials.

The further embodiment of the invention describes the orthogonally compatible solid support, thus obtained was found to have optimum functionality (0.3–0.5 meq/g) and the new resin 1, was found to be stable at ambient temperature for several months and once prepared, can be used for a long time for the subsequent synthetic applications without any special storage conditions.

In another embodiment of the invention comprises that the resin bearing amino acid was tested for stability towards the reagents and experimental conditions commonly used for peptide synthesis during Boc and Fmoc chemistry protocols and found stable under 50% TFA:DCM as well as 20% piperidine in DMF excessively used in solid phase peptide synthesis.

In yet another embodiment, the solid support is used for solid phase synthesis of peptides, protected peptide fragments and small organic molecules.

In yet another embodiment, orthogonally compatible, hydroxyethyl-sulphenyl-acetamido (HESA) resin is used for solid phase synthesis of peptides through Boc chemistry protocol.

In yet another embodiment, orthogonally compatible, hydroxyethyl-sulphenyl-acetamido (HESA) resin is used for solid phase synthesis of peptides through Fmoc chemistry protocol.

In yet another embodiment, the orthogonally compatible, hydroxyethyl-sulphenyl-acetamido (HESA) resin is used for solid phase synthesis of peptides through both the Boc and Fmoc chemistry protocol separately or in combination.

In yet another embodiment, the hydroxyethyl-sulphenyl-acetamido-Resin is used for the solid phase synthesis of heterocyclic small organic molecules such as thiazolidine derivatives.

In yet another embodiment, the hydroxyethyl-sulphenyl-acetamido-Resin is used for the solid phase synthesis of small organic molecule combinatorial libraries.

In yet another embodiment, the final products are cleavable under mild alkaline conditions.

In yet another embodiment, the final products are cleaved from the solid support using a mixture of 0.1–0.5 N aq. alkali and organic solvents selected from the group consisting of dioxane, tetrahydrofuran, methanol, ethanol and dimethylformamide.

In yet another embodiment, the solid support is also used as scavenger resin and immobilized reagents after suitable modification wherein the functional groups are selected from the group comprising aldehyde, carboxylic, thiol, amino and polyamino groups.

In yet another embodiment, the reactions are carried out in the presence of organic solvents selected from the group comprising methylene chloride, tetrahydrofuran, dimethylformamide, ether, petroleum ether, acetic acid, methanol etc. in the presence of N,N'-dicyclohexylcarbodiimide, 1-hydroxybenzotriazole, N-hydroxysuccinimide etc. at temperatures ranging between 15° C. and 85° C.

In yet another embodiment, the reactions is performed using coupling reagents selected from the group comprising dicyclohexylcarbodiimde, mixed anhydride, active esters, benzotriazole-1-yl-oxy-tris-(dimethylamino)phosphonium hexa fluorophospahte (BOP), benzotriazole-1-yl tetramethyluronium hexafluoro phosphate (HBTU) or 7-azabenzotriazole-1-yl tetramethyluronium hexafluorophosphate (HATU).

In yet another embodiment, acids used for acidolytic cleavage of the protecting groups are selected from the group comprising, HBr:AcOH, HCl:Dioxane, formic acid and trifluoroacetic acid.

In yet another embodiment feature of the invention is that racemization free products are obtained. Further, the invention also provides a process for the synthesis of peptides using both Boc and Fmoc chemistry protocols separately or in combination and solid phase synthesis of small organic molecules such as thiazolidine derivatives [FIGS. IV–VII as shown in the accompanying drawings]. The final products, after the solid phase synthesis, can be cleaved from the solid support under very mild conditions. The present invention also describes the synthesis of peptides and small molecules for generation of combinatorial libraries in good yields and purity using the new solid support.

The invention will be further described by reference to the following detailed examples. These examples are offered to further illustrate the various specific and illustrative embodiments and techniques and should not be construed to limit the scope of the present invention.

Experimental Section:

General Methods

All the amino acids, used for the present study were of L-configuration, unless stated otherwise. The support used was, 2% cross linked, aminomethylated styrene/divinylbenzene co-polymer having substitution 0.5–0.9 meq/g. All coupling reactions were carried out with anhydrous reactants and dry solvents. Homogeneity of all the intermediates and final compounds was established by TLC on silica gel plates using the following solvent systems: (a) $CHCl_3$-MeOH-AcOH (49:1:1), (b) $CHCl_3$-MeOH (19:1), (c) $CHCl_3$-MeOH-AcOH (48:1:1), (d) $CHCl_3$-MeOH-AcOH (18:1:1), (e) $CHCl_3$-MeOH-AcOH (17:2:1), (f) n-BuOH-AcOH-$H_2O$ (4:1:5, upper layer). Purity of the final compounds was also checked by RP-HPLC using μ-Bondapak $C_{18}$ column and a linear gradient 0–40% B in 40 min (A=0.1% aqueous TFA, B=Acetonitrile) and monitored at 225 nm (UV). Optical rotations were recorded on a Perkin Elmer 241 polarimeter. NMR spectra were recorded on Bruker DRX 300 MHz spectrometer. IR spectra were recorded on Shimadzu 8201PC FTIR.

EXAMPLE 1

Synthesis of Hydroxyethyl-sulphenyl-acetamido-resin (Compound 1)

Commercially available amino methyl polystyrene resin 2.0 g (0.9 meq/g) was placed in solid phase reaction vessel and dry dichloromethane (DCM) was added to it. This suspension was allowed to swell under nitrogen stirring for 30 min. This was washed with DCM thrice and once with a mixture of DCM:DMF (1:1). It was treated with chloroacetic acid (0.45 g, 5 mmol) and DIC (0.8 ml, 5 mmol) in the presence of catalytic amount of dimethylaminopyridine (DMAP) in DCM:DMF (1:1). The reaction mixture was stirred under nitrogen for 8 h or till negative to Kaiser test. The resin was filtered, washed successively with 25 ml each of DMF, DCM:DMF (1:1), DMF, DCM:DMF (1:1), and finally with DCM. The resin, having chloroacetyl handle was allowed to react under nitrogen stirring with a solution of mercaptoethanol (0.4 ml, 5 mmol) in 20 ml of DCM:DMF (1:1) for 6–8 hrs in the presence of tertiary amine and sodium iodide as catalyst. The resin was filtered washed three times with DCM:DMF (1:1) and finally DCM and dried to get the desired resin 1 (2.1 g).

Characterization of the Solid Support

The new linker based solid support 1 was characterized on the basis of a strong peak at 1666 cm$^{-1}$ corresponding to the carbonyl of the newly introduced acetamido moiety and a peak at 3219 cm$^{-1}$ corresponding to the primary hydroxy group.

Determination of Degree of Substitution

The quantitation of the hydroxy functional group was carried out by the standard procedures reported in the literature by loading the appropriate Boc or Fmoc protected amino acids employing standard protocol. In case of the Boc-chemistry, the quantitation was carried out using picric acid method [Method A]. Whereas in the case of Fmoc chemistry, the Fmoc group was removed by the piperidine treatment and subsequently measuring the absorbance at 301 nm [Method B] quantitated the 9-fluorenylmethyl piperidine. The degree of substitution of the new linker was observed between 0.35–0.45 meq/g. Details are given below;

Method A: (Boc Chemistry)

The hydroyethyl-sulphenyl-acetamido resin (1) (0.5 g) was placed in reaction vessel and allowed to swell in dichloromethane (DCM) under nitrogen stirring. After 30 min. the resin was filtered and washed with DCM. To this resin a solution of Boc-Leu (0.42 g, 2.4 mmol), DIC (0.2 ml, 2.5 mmol) and dimethylaminopyridine (DMAP) or N-methyl imidazole (NMI) (0.4 mmol) in DCM:DMF (1:1) 20 ml was added. This mixture was stirred for 8–10 hrs. The resin was washed three times with DCM and dried. An aliquot of the dried resin (~30.0 mg) was subjected to acidolysis (5N.HCl/dioxan, 5 ml) for 30 min to remove Boc-group. After this, the resin was washed with DCM and DMF. Shaking with DIEA (2 ml) in DCM-DMF (1:1) (40 ml) neutralized the hydrochloride salt so obtained. The resin was then washed successively with DMF and DCM. The above product was then quantitated by picric acid method to find out the amount of amino groups on the solid support. An aliquot (2.5 mg) of the resin was taken and stirred with picric acid (50 mg) in DCM (2 ml) and ethanol (8 ml). After washing the resin thoroughly it was stirred with DIEA (1 ml) as a result of which the picric acid attached to the resin was released in the solution as its DIEA salt. The solution was made up to 50 ml and the absorbance recorded at 350 nm using an UV spectrophotometer. The following formula was used for calculation.

$$\mu M/g = \frac{OD \text{ at } 358 \text{ nm} \times \text{Vol. of solution made in ml}}{E \times \text{wt. of resin used in mg}} \times 10^6$$

Method B: (Fmoc Chemistry)

The hydroxyethyl-sulphenyl-acetamido-resin (1) (0.5 g) was placed in reaction vessel and allowed to swell in dichloromethane (DCM) under nitrogen stirring. After 30 min. the resin was filtered and washed with DCM. To this resin a solution of Fmoc-Leu (0.82 g, 2.4 mmol), DIC (0.2 ml, 2.5 mmol) and dimethylaminopyridine (DMAP) or N-methyl imidazole (NMI) (0.4 mmol) in DCM:DMF (1:1) 20 ml and was added. This mixture was stirred for 8–10 hrs. The resin was washed three times with DCM and dried. An aliquot of this dried Fmoc-Leu-resin (2.5 mg) was taken in a test tube and treated with 0.5 ml of 20% piperidine in DMF for 15–20 min with occasional vortex shaking. In a separate tube 0.5 ml 20% piperidine in DMF was taken as reference. After 20 min DMF was added to both the tubes to bring to a volume of 50 ml. The absorbance of both the solutions is recorded by an UV-VIS spectrophotometer at 301 nm. The degree of substitution (mMol/g) is calculated by following formula.

$$mMol/g = \frac{A_{301} \times \text{Vol (mL)}}{7800 \times \text{wt (g)}}$$

Stability Studies:

In order to demonstrate the stability of the linker during deblocking of Boc and/or Fmoc protecting groups under extended exposure with reagents following experiments were done. Small aliquots of Fmoc protected amino acid bound to the solid support (0.41 meq/g, 100 mg) was separately treated under stirring with 1 ml each of 50% TFA in DCM and SN. HCl/dioxane for 8 hrs and then the resins were filtered, washed and dried. I an separate flask Boc protected amino acid bound to the solid support (0.38 meq/g, 120 mg) was treated under stirring with 1.2 ml of 20% piperidine/DMF for 10 hrs and then the resin was filtered, washed and dried. The dried resins were quantitated using methods A and B and the results were almost identical with the untreated resins, thereby suggesting that the linker is stable to the conditions employed for the deprotection of Fmoc and Boc groups.

Racemization Studies

The dipeptides as described in examples 6 & 7 synthesized on the new base labile solid support were used as substrate to detect any racemization resulted during synthesis and cleavage of the product from the solid support.

Boc-Gly-L-Phe-OH (6) and Boc-Gly-D-Phe-OH (7), 0.0064 g (20 μM) each, were dissolved in 1M NaCl (50 μl) in separate reaction vials and 1M tris HCl (50 μl) was added to it to maintain the pH at 7.5. 15–50 μl of carboxypeptidase-A were added in different set of experiments in each of the vials and shaken at 25° C. for 5 min. An aliquot of the reaction mixture before and after 5 min of addition of enzyme were then analyzed by RP-HPLC using a linear gradient of 0–90% acetonitrile in water containing 0.1% TFA over 40 min. Boc-Gly-L-Phe-OH as well as Boc-Gly-D-Phe-OH showed a retention time of 12.5 and 13 min respectively while Boc-Gly-L-Phe-OH after enzymatic hydrolysis gave no peak at the retention time of dipeptide but instead gave another peak at the retention time of 8 min, corresponding to Boc-Gly. Whereas HPLC profile of the Boc-Gly-D-Phe-OH after treatment with the enzyme showed no change in retention time from that of dipeptide before hydrolysis i.e. 13 min.

EXAMPLE 2

Synthesis of Tyr-Gly-Gly-Phe-Leu-OH
(Compound 2)

The solid support, hydroxyethyl-sulphenyl-acetamido-resin (1), (1.25 g, 0.5 mmol) having substitution 0.4 meq/g was placed in reaction vessel and allowed to swell in dichloromethane (DCM) under nitrogen stirring. After 30 min. the resin was filtered and washed with DCM. To this resin a solution of Boc-Leu (0.25 g, 1.2 mmol) dimethylaminopyridine (DMAP) or N-methyl imidazole (NMI) (0.2 mmol) in DCM:DMF (1:1) 20 ml and was added. This mixture was stirred for 8–10 hrs. The resin was washed three times with DCM and dried. An aliquot of this dried resin (2.5 mg) was tested for the loading and the loading was found to be 78% [Method B]. The resin was treated with 50% TFA in DCM for 30 min. to remove Boc group. After 30 min the resin was filtered and washed with DCM 20 ml×3, 20% DIEA in DCM 20 ml×3, DCM 20 ml×3. A solution of Boc-Phe (0.26 g, 1 mmol) and HOBt (0.153 g, 1 mmol) in DCM:DMF (1:1) 20 ml was added to the above resin under nitrogen stirring. To this suspension DIC (0.18 ml, 1.2 mmol) was added and the mixture was stirred for 3 hrs or till the resin was negative to Kaiser test.

The resin was treated with 50% TFA in DCM for 30 min. to remove Boc group. The resin was filtered and washed with DCM 20 ml×3, 20% DIEA in DCM 20 ml×3, DCM 20 ml×3 and the resin having free amino group was coupled with Boc-Gly by DIC/HOBt procedure. After complete coupling reaction, the resin was filtered and treated with 50% TFA in DCM to remove Boc group in a usual manner and coupled with Boc-Gly. After complete coupling reaction as monitored by Kaiser test the Boc group was removed in a usual manner and subsequently coupled with Boc-Tyr using DIC/HOBt procedure. The resin having pentapeptide was treated with a mixture of dioxan-MeOH-4N. NaOH (30:9:1, 20 ml) for 30 min under nitrogen stirring and the resin was filtered and washed with 2 ml of water. The combined filtrate was evaporated in vacuo. The residue was taken in water and extracted with ether. The aqueous layer acidified with 1N hydrochloric acid and extracted with EtOAc (3×75 ml). The combined EtOAc layer was washed with water and brine then dried over $Na_2SO_4$ and evaporated in vacuo to get an amorphous solid. The crude pentapeptide acid, thus obtained, was recrystallized from MeOH-ether to afford 0.21 g of the title compound. Yield: 83% $R_f$: 0.8(d); m.p. 134–136° C.; $[\alpha]_D^{25}$=−9.8° (c=4.1, MeOH); $^1$H NMR (DMSO-$d_6$) δ: 0.97 (d, 6H), 1.16 (s, 9H), 3.6–3.8(m, 4H), 4.10, 4.24 and 4.58 ($C^\alpha$ protons), 6.63–7.00 (ABq, 4H), 7.40(m, 5H), 7.8–8.1 (NHs). The peptide acid (0.21 g, 0.3 mmol), obtained above, was stirred in 5N.HCl/dioxan (2 ml) for 1 h in the presence of thioanisole (0.2 ml). After monitoring the reaction by TLC the solvent was evaporated in vacuo. On addition of dry ether and triturating, the pentapeptide hydrochloride HCl. Tyr-Gly-Gly-Phe-Leu-OH (2) was obtained as white hygroscopic solid. It was filtered and dried in a vacuum desiccator. Yield: 0.15 g (85%); $R_f$: 0.67(F); m.p.141° C. (dec); $[\alpha]_D^{25}$=−5.6° (c=0.54, MeOH); FAB-MS [M+H]$^+$ 556; $^1$H NMR (DMSO-$d_6$) δ: 0.9 (d, 6H), 3.8–3.9 (m, 4H), 4.2, 4.3, and 4.68 ($C^\alpha$ protons), 6.8–7.1 (ABq, 4H), 7.3 (m, 5H), 7.5–8.5 (NHs), 9.0 (s, 1H, phenolic OH).

EXAMPLE 3

Synthesis of Tyr-D-Ala-Gly-Phe-Leu-OH
(Compound 3)

The solid support, hydroxyethyl-sulphenyl-acetamido-resin (1), (0.75 g, 0.3 mmol) having substitution 0.4 meq/g was placed in reaction vessel and allowed to swell in dichloromethane (DCM) under nitrogen stirring. After 30 min. the resin was filtered and washed with DCM. To this resin, a solution of Boc-Leu was attached using 3 molar excess in a usual manner. An aliquot of this resin (3.4 mg) was tested for the loading and the loading was found to be 81% [Method B]. Subsequently, synthesis of Boc-Tyr-D-Ala-Gly-Phe-Leu-OH has been carried out in a manner similar to that applied for getting Boc-Tyr-Gly-Gly-Phe-Leu-OH by substituting Boc-D-Ala instead of Boc-Gly at position 2. After cleavage from the solid support, Boc-Tyr-Gly-Gly-Phe-Leu-OH (0.13 g, 79%) was isolated as white powder. This was then treated with 5N.HCl-dioxan(2 ml) for 1 h in the presence of thioanisole (0.1 ml). After monitoring the reaction by TLC the solvent was evaporated and the residue triturated with dry ether. It was then filtered and dried in a vacuum desiccator to afford 0.16 g (82.8%) of the final peptide HCl.Tyr-D-Ala-Gly-Phe-Leu-OH as a white solid. $R_f$: 0.48 (F); m.p.183° C. (dec.); $[\alpha]D^{25}$=+14.3° (c=0.56, MeOH); Yield: 0.15 g (85%); $R_f$: 0.67(F); m.p.141° C. (dec); $[\alpha]D^{25}$=−5.6° (c=0.54). $^1$H NMR δ: 0.85 (d, 6H), 1.02 (d, 3H), 3.6 (d, 2H,), 4.26, 4.38, 4.44 and 4.68 ($C^\alpha$ protons), 6.8–7.0 (ABq, 4H), 7.24 (m, 5H), 7.5–8.5 (NHs), 9.05 (s, 1H, phenolic OH).

EXAMPLE 4

Synthesis of Tyr-Gly-Gly-Phe-Leu-OH
(Compound 2 through Fmoc-Chemistry)

The hydroyethyl-sulphenyl-acetamido-resin (1) (0.1 g, 0.4 mmol) having substitution 0.4 meq/g was placed in reaction vessel and allowed to swell in dichloromethane (DCM) under nitrogen stirring. After 30 min. the resin was filtered and washed with DCM. To this resin a solution of Fmoc-Leu (0.41 g, 1.2 mmol), DIC (0.2 ml, 1.5 mmol) and dimethylaminopyridine (DMAP) or N-methyl imidazole (NMI) (0.2 mmol) in DCM:DMF (1:1) 20 ml and was added. This mixture was stirred for 8–10 hrs. The resin was washed three times with DCM and dried. An aliquot of this dried resin (2.5 mg) was tested for the loading and the loading was found to be 78% [Method A]. The resin was treated 20% piperidine in DCM:DMF (1:1) 12 ml for 20 min to remove Fmoc group. The resin was washed three times with DCM. After washing the resin with DCM three times, a solution of Fmoc-Phe (0.38 g 1.0 mmol) and HOBt (0.15 g 1.0 mmol) in DCM:DMF (1:1) 10 ml was added under stirring. To this mixture DIC (0.18 ml, 1.2 mmol) was added and the stirring was continued for 3 hrs or till it was negative to Kaiser test. The resin was filtered and washed with DCM 20 ml×3 times. The Fmoc group was deblocked by the treatment with 20% piperidine in DCM:DMF (1:1) 12 ml for 20 min in a usual manner. Subsequently, Fmoc-Gly(step 3 of FIG. V), Fmoc-Gly (step 4 of FIG. V) were then coupled by DIC/HOBt method as described above. The Boc-Tyr was used instead of Fmoc-Tyr for the last coupling. The resin having pentapeptide was treated with a mixture of dioxan-MeOH-4N. NaOH (30:9:1, 20 ml) for 30 min under nitrogen stirring and the resin was filtered and washed with 2 ml of water. The combined filtrate was evaporated in vacuo. The residue was taken in water and extracted with ether. The aqueous layer acidified with 1N hydrochloric acid and extracted with EtOAc (3×75 ml). The combined EtOAc layer was washed with water and brine then dried over $Na_2SO_4$ and evaporated in vacuo to get an amorphous solid. The crude penta peptide acid, thus obtained, was recrystallized from MeOH-ether to afford the title compound. Yield: 0.16g, (77%) $R_f$: 0.8(d); m.p. 140–141° C. (dec); $[\alpha]_D^{25}$=−5.6° (c=0.54, MeOH); FAB-MS [M+H]$^+$570; $^1$H NMR (DMSO-d$_6$) δ: 0.91 (d, 6H), 3.8–3.9 (m, 4H), 4.26, 4.37, and 4.60 (C$^\alpha$ protons), 6.8–7.1 (ABq, 4H), 7.30 (m, 5H), 7.5–8.5 (NHs), 9.05 (s, 1H, phenolic OH).

EXAMPLE 5

Synthesis of Lys-Thr-Thr-Lys-Ser-OH (Compound 5)

Boc-Ser(Bzl) was attached to the hydroyethyl-sulphenyl-acetamido-resin following the standard procedure. The solid support (0.73 g, 0.25 mmol) having substitution 0.34 meq/g was placed in reaction vessel and allowed swelling in dichloromethane (DCM) under nitrogen stirring. After 30 min. the resin was filtered and washed with DCM. To this resin a solution of Boc-Ser(Bzl) (0.30 g, 1.0 mmol) dimethylaminopyridine (DMAP) or N-methyl imidazole (NMI) (0.2 mmol) in DCM:DMF (1:1) 15 ml and was added. Subsequently, DIC (0.16 ml, 1 mmol) was added to the reaction mixture. This mixture was stirred for 8–10 hrs. The resin was washed three times with DCM and dried. An aliquot of this dried resin (2.0 mg) was tested for the loading and the loading was found to be 81% [Method B]. The resin was treated with 50% TFA in DCM for 30 min. to remove Boc group. After 30 min the resin was filtered and washed with DCM 20 ml×3, 20% DIEA in DCM 20 ml×3, DCM 20 ml×3. The resin having free amino group of Boc-Lys(Cl-Z) was coupled with the other in coming amino acids viz. Boc-Lys(2-Cl-Z), Boc-Thr(Bzl), Boc-Thr(Bzl) and finally Boc-Lys(2-Cl-Z) were then coupled successively to the growing peptide chain. Deblocking of Boc group at each step was carried out using 50% TFA in $CH_2Cl_2$. The final protected peptide Boc-Lys(2-Cl-Z)-Thr(Bzl)-Thr(Bzl)-Lys (2-Cl-Z)-Ser(Bzl)-OH was then obtained by treating the resin with 0.1 N NaOH. Protected peptide was then subjected to catalytic transfer hydrogenation using Pd/C to get Boc-Lys-Thr-Thr-Lys-Ser-OH. Boc group at the final step was removed using 5N.HCl in dioxane to afford the final peptide Lys-Thr-Thr-Lys-Ser-OH. Yield 0.09 g, (78.5%); Rf 0.33 (F); m.p. 158° C.; FAB-MS, [M+H]$^+$ 564; $[\alpha]_D^{25}$=+20° (c=0.1, DMF); $^1$H NMR (DMSO-d$_6$) δ: 1.06 (d, 3H), 1.10 (d, 3H), 1.36 (m, 2H), 1.53 (m, 2H), 2.73 (t, 4H), 4.15 (m, 2H), 4.16–4.4 (C$^\alpha$Hs),7.49 (t, 3H), 7.59 (t, 3H), 7.8–8.70 (NHs).

EXAMPLE 6

Synthesis of Boc-Gly-L-Phe-OH (Compound 6)

The title compound was synthesized (0.5 mmol scale) on the above mentioned base labile linker attached to the solid support in a manner similar to that employed for getting 2. Yield 0.10 g (76%); $R_f$ 0.34 (a); m.p.118° C.; $[\alpha]_D^{25}$=+40° (c=0.11, DMF); FAB-MS [M+H]$^+$ 323; $^1$H NMR (DMSO-d$_6$) δ: 1.16(s, 9H), 2.3(m, 2H), 3.6 (m, 2H), 4.58 (bs, 1H), 7.4 (m,5H), 7.9–8.2 (NHs).

EXAMPLE 7

Boc-Gly-D-Phe-OH (Compound 7)

Similarly, compound 7 was also synthesized on 0.5 mmol scale Yield: 0.12 g (80%); $R_f$ 0.34 (a); m.p. 109° C.; $[\alpha]_D^{25}$=+50° (c=0.11). FAB-MS [M+H]$^+$ 323; $^1$H NMR (DMSO-d$_6$) δ1.16(s, 9H), 2.3(m, 2H), 3.6 (m, 2H), 4.58 (bs, 1H), 7.4 (m, 5H), 7.9–8.2 (NHs).

EXAMPLE 8

Synthesis of 2-(4-Methoxyphenyl)thiazolidine-4-carboxylic Acid (Compound 8)

Commercially available Fmoc-Cys(Trt) was attached to the linker based solid support 1 by DIC/DMAP procedure. The solid support (1.0 g) having substitution 0.4 meq/g was placed in reaction vessel and allowed to swell in dichloromethane (DCM) under nitrogen stirring. After 30 min. the resin was filtered and washed with DCM. To this resin a solution of Fmoc-Cys(Trt) (0.70 g, 1.2 mmol) dimethylaminopyridine (DMAP) or N-methyl imidazole (NMI) (0.4 mmol) in DCM:DMF (1:1) 20 ml and was added. This mixture was stirred for 8–10 hrs. The resin was washed three times with DCM and dried. An aliquot of this resin was tested to check the loading by the treatment with 20% piperidine and subsequently recording the absorbance in UV [Method A]. It came out to be 90% loading. The resin bearing Fmoc-Cys(Trt) was treated with 20% piperidine in DCM:DMF (1:1) 20 ml for 20 min to remove Fmoc group. The resin was washed three times with DCM and then treated with 10% trifluoric acid (TFA)/Bu$_3$SiH in DCM for 30 min (three times) to remove the trityl group of Cys. After washing the resin with DCM 3 times, a solution of p-anisaldehyde (0.5 ml) in DCM:DMF (1:1) 15 ml was added under stirring and the stirring was continued for 8–10 hrs. The resin was washed three times with DCM and dried. It was treated with a mixture of dioxan-MeOH-4N. NaOH (30:9:1, 20 ml) for 30 min under stirring and the resin was filtered and washed with 2 ml of water. The combined filtrate was evaporated in vacuo. The residue was taken in water and extracted with ether. The aqueous layer acidified with 1N hydrochloric acid and extracted with EtOAc (3×70 ml). The combined EtOAc layer was washed with water and brine then dried over $Na_2SO_4$ and evaporated in vacuo to yield 2-(4-methoxyphenyl) thiazolidine-4-carboxylic acid as white crystalline material. Yield: 0.061 g, 72%; m.p. 150–51° C.; FAB-MS [M+H]$^+$ 239; $^1$H NMR (DMSO-d$_6$) δ: 3.5 (m, 2H), 3.7 (s, 3H), 4.8 (bs, 1H), 5.9 (bs, 1H), 6.8–7.1 (Abq, 4H).

EXAMPLE 9

Synthesis of N-Boc-2-(4-methoxyphenyl) thiazolidine-4-carboxylic Acid (Compound 9)

Commercially available Fmoc-Cys(Trt) was attached to the linker based solid support # by DIC/DMAP procedure. The solid support (0.50 g) having substitution 0.34 meq/g was placed in reaction vessel and allowed to swell in dichloromethane (DCM) under nitrogen stirring. After 30 min. the resin was filtered and washed with DCM. To this resin a solution of Fmoc-Cys(Trt) (0.56 g, 1.0 mmol) dimethylaminopyridine (DMAP) or N-methyl imidazole (NMI) (0.25 mmol) in DCM:DMF (1:1) 20 ml and was added. This mixture was stirred for 8–10 hrs. The resin was washed three times with DCM and dried. An aliquot of this resin was tested to check the loading by treatment with 20% piperidine and subsequently recording the absorbance indicating approximately 88% loading [Method A]. The resin bearing Fmoc-Cys(Trt) was treated 20% piperidine in DCM:DMF (1:1) 12 ml for 20 min to remove Fmoc group. The resin was washed three times with DCM and then treated with 10% trifluoric acid (TFA)/Bu$_3$SiH in DCM for 30 min (three times) to remove the trytyl group of Cys. After washing the resin with DCM 3 times, a solution of p-anisaldehyde (0.5 ml) in DCM:DMF (1:1) 10 ml was added under stirring. The stirring was continued for 8–10 hrs. The resin was washed three times with DCM. To this resin, a solution of di-tert-butyldicarbonate (0.22 g, 1 mmol) and DIEA (0.2 ml, 1.0 mmol) in DCM:DMF (1:1) 10 ml were added and the stirring were continued for three hrs. After three hours the resin was negative to Kaiser test. The resin was washed with DCM:DMF (1:1) 10 ml×3, with DMF 10 ml×3, DCM:DMF (1:1) 10 ml×2 and finally three times with DCM and dried. It was treated with a mixture of dioxan-MeOH-4N. NaOH (30:9:1, 20 ml) for 30 min under stirring and the resin was filtered and washed with 2 ml of water. The combined filtrate was evaporated in vacuo. The residue was taken in water and extracted with ether. The aqueous layer acidified with 1N hydrochloric acid and extracted with EtOAc (3×70 ml). The combined EtOAc layer was washed with water and brine then dried over Na$_2$SO$_4$ and evaporated in vacuo to yield N-Boc-2-(4-methoxyphenyl)thiazolidine-4-carboxylic acid as white crystalline material. Yield: 0.048 g, 82%; m.p. 160–162° C.; FAB-MS [M+H]$^+$ 340. $^1$H NMR (DMSO-d$_6$) δ: 1.2 (s, 9H), 3.4 (m, 2H), 3.9 (s, 3H), 4.7 (bs, 1H), 5.9 (bs, 1H), 6.8–7.1 (Abq, 4H).

EXAMPLE 10

Synthesis of N-Benzoyl-2-(4-methoxyphenyl) thiazolidine-4-carboxylic Acid (Compound 10)

Commercially available Fmoc-Cys(Trt) was attached to the linker based solid support # by DIC/DMAP procedure. The solid support (0.50 g) having substitution 0.34 meq/g was placed in reaction vessel and allowed to swell in dichloromethane (DCM) under nitrogen stirring. After 30 min. the resin was filtered and washed with DCM. To this resin a solution of Fmoc-Cys(Trt) (0.56 g, 1.0 mmol) dimethylaminopyridine (DMAP) or N-methyl imidazole (NMI) (0.25 mmol) in DCM:DMF (1:1) 20 ml were added. This mixture was stirred for 8–10 hrs. An aliquot of the resin was washed three times with DCM and dried. An aliquot of this resin was tested to check the loading by the treatment with 20% piperidine and subsequently recording the absorbance indicating approximately 88% loading [Method A]. The resin bearing Fmoc-Cys(Trt) was treated 20% piperidine in DCM:DMF (1:1) 12 ml for 20 min to remove Fmoc group. The resin was washed three times with DCM and then treated with 10% trifluroacetic acid (TFA)/Bu$_3$SiH in DCM for 30 min (three times) to remove the trityl group of Cys. After washing the resin with DCM 3 times, a solution of p-anisaldehyde (0.5 ml) in DCM:DMF (1:1) 10 ml was added under stirring. The stirring was continued for 8–10 hrs. The resin was washed three times with DCM. To this resin, a solution of Benzoyl chloride (0.2 ml, 2 mmol) and DIEA (0.4 ml, 2.0 mmol) in DCM:DMF (1:1) 10 ml were added and the stirring was continued for 3 hrs until the resin was negative to Kaiser test. The resin was washed with DCM:DMF (1:1) 10 ml×3, with DMF 10 ml×3, DCM:DMF (1:1) 10 ml×2 and finally three times with DCM and dried. It was treated with a mixture of dioxan-MeOH-4N. NaOH (30:9:1, 20 ml) for 30 min under stirring and the resin was filtered and washed with 2 ml of water. The combined filtrate was evaporated in vacuo. The residue was taken in water and extracted with ether. The aqueous layer acidified with 1N hydrochloric acid and extracted with EtOAc (3×70 ml). The combined EtOAc layer was washed with water and brine then dried over Na$_2$SO$_4$ and evaporated in vacuo to yield N-Benzoyl-2-(4-methoxyphenyl)thiazolidine-4-carboxylic acid as white crystalline material. Yield: 0.043 g, 72%; m.p. 108–110° C.; FAB-MS [M+H]$^+$ 344; $^1$H NMR (DMSO-d$_6$) δ: 3.3 (m, 2H), 3.9 (s, 3H), 4.7 (bs, 1H), 5.7 (bs, 1H), 6.6 (m 5H), 6.9–7.2 (Abq, 4H).

EXAMPLE 11

Synthesis of N-Boc-2-(4-methoxyphenyl) thiazolidinyl-leucine (Compound 11)

The new linker based solid support 1 (1.0 g) having substitution 0.4 meq/g was placed in reaction vessel and allowed to swell in dichloromethane (DCM) under nitrogen stirring. After 30 min. the resin was filtered and washed with DCM. To this resin a solution of Boc-Leu (0.45 g, 2 mmol) dimethylaminopyridine (DMAP) or N-methyl imidazole (NMI) (0.4 mmol) in DCM:DMF (1:1) 20 ml and was added. The reaction mixture was stirred for 8–10 hrs. The resin was washed three times with DCM and dried. An aliquot of this dried resin (2.5 mg) was tested for the loading and the loading was found to be 82% [Method B]. The resin was treated with 50% TFA in DCM for 30 min. to remove Boc group. After 30 min the resin was filtered and washed with DCM 20 ml×3, 20% DIEA in DCM 20 ml×3, DCM 20 ml×3 and finally suspended in 20% piperidine solution DMF:DCM (1:1) 20 ml and treated with DCM:DMF (1:1) 20 ml. The resin having free amino group of Leu, was reacted with a solution of Boc-Cys-(Trt) (0.56 g, 1 mmol) and HOBt (0.153 g, 1 mmol) in DCM:DMF (1:1) 20 ml under nitrogen stirring. To this suspension DIC (0.18 ml, 1.2 mmol) was added and the mixture was stirred for 3 hrs until the resin was negative to Kaiser test. It was filtered and washed with DCM:DMF (1:1) 15 ml×3 and finally with DCM. The resin was treated with 50% trifluoroacetic acid (TFA)/Bu$_3$SiH in DCM for 30 min and then washed with 10% trifluoric acid (TFA)/Bu$_3$SiH in DCM for 10 min (three times) to remove both Boc and trytyl group of Cys. After washing the resin with DCM 3 times, a solution of p-anisaldehyde (0.5 ml) in DCM:DMF (1:1) 10 ml was added under stirring. The stirring was continued for 8–10 hrs. The resin was washed three times with DCM. To this resin, a solution of Benzoyl chloride (0.2 ml, 2 mmol) and DIEA (0.4 ml, 2.0 mmol) in DCM:DMF (1:1) 10 ml were added and the stirring were continued for three hrs. After three hours, the resin was negative to Kaiser test. The resin was washed with DCM:DMF (1:1) 10 ml×3, with DMF 10 ml×3, DCM:DMF (1:1) 10 ml×2 and finally three times with DCM and dried. It was treated with a mixture of dioxan-MeOH-4N. NaOH (30:9:1, 20 ml) for 30 min under stirring and the resin was filtered and washed with 2 ml of water. The combined filtrate was evaporated in vacuo. The residue was taken in water and extracted with ether. The aqueous layer acidified with 1N hydrochloric acid to pH 2.0 and extracted with EtOAc (3×70 ml). The combined EtOAc layer was washed with water and brine then dried over Na$_2$SO$_4$ and evaporated in vacuo to yield N-Boc-2-(4-methoxyphenyl) thiazolidinyl-leucine as a glassy material. Yield: 0.11 g, 78%; FAB-MS [M+H]$^+$ 453; $^1$H NMR (DMSO-d$_6$) δ: 0.9 (m, 6H), 1.2 (bs, 9H), 1.7 (m, 2H), 4.3 (m 1H), 3.5 (m, 2H), 3.7 (s, 3H), 4.86 (bs, 1H), 5.9 (bs, 1H), 6.8–7.1 (Abq, 4H).

ADVANTAGES OF THE INVENTION

The new linker based solid support, hydroyethyl-sulphenyl-acetamido resin (HESA resin) as shown in formula 1 FIG. I, is orthogonally compatible solid support for the peptide synthesis viz. it can be use for the synthesis of biologically active peptides using both Boc and Fmoc chemistry separately or in combination. Since it requires a very mild basic condition for the cleavage of the products from the support, it offers rapid synthesis of protected peptides fragments, which are useful for the convergent synthesis of large peptides. The peptides synthesized are of high yield and excellent purity. Further the products are free from racemization. This also allows synthesis of sequences with oxidation prone amino acids at the C-terminus. The new linker based support can be used for the solid phase synthesis of small organic molecules and generation of combinatorial libraries of peptides and small organic as well as heterocyclic molecules. The new solid support can be synthesized very conveniently in the laboratory in bulk and does not require any special precaution during storage and can be stored for months at ambient temperature for subsequent synthetic applications. Further, a new and novel method has also been developed for its synthesis.

What is claimed is:

1. An orthogonally compatible, hydroxyethyl-sulphinyl-acetamido resin of formula 1 for use in peptide synthesis and combinatorial library synthesis, wherein the formula 1 is shown below:

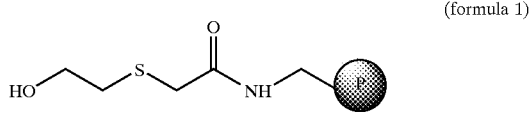

(formula 1)

and wherein P represents an amino methyl resin.

2. A resin of the formula 1 as claimed in claim 1, wherein said resin of the formula 1 forms a solid support, wherein the solid support further comprises a material selected from the group consisting of amino-functional membranes, porous glass, silica, polystyrenes, polydimethylacrylamides, cotton, and paper.

3. A resin of the formula 1 as claimed in claim 2, wherein the polystyrenes are selected from the group consisting of aminopolystyrene and aminomethyl polystyrene.

4. A resin of the formula 1 as claimed in claim 1, wherein said resin of the formula 1 is used for solid phase peptide/oligonucleotide synthesis.

5. A resin of the formula 1 as claimed in claim 1, wherein the resin of the formula 1 forms a solid support and wherein final products are cleaved from the solid support under mild alkaline conditions.

6. A resin of the formula 1 as claimed in claim 1, wherein the resin of the formula 1 forms a solid support and wherein final products are cleaved from the solid support using a mixture of 0.1–0.5 N aq. alkali and organic solvents selected from the group consisting of dioxane, tetrahydrofuran, methanol, ethanol, and dimethylformamide.

7. A resin of the formula 1 as claimed in claim 1, wherein the resin of the formula 1 forms a solid support having functional groups, wherein the solid support is used as scavenger resin and is treated with immobilized reagents after modification of the functional groups, wherein the functional groups are selected from the group consisting of aldehyde, carboxylic, thiol, amino, and polyamino groups.

8. A method for synthesizing the resin of the formula 1 as claimed in claim 1, wherein the method comprises the steps of:

i) reacting chloroacetic acid, or its equivalent containing a an easy leaving group in place of halogen, with an amino methyl resin in the presence of diisopropylcarbodiimide or any other commonly used coupling reagent to yield a first solid support, and ii) reacting the first solid support having a leaving group with mercaptoethanol in presence of sodium iodide to yield the resin of the formula 1, wherein the resin of the formula 1 forms a desired solid support for use in organic synthesis.

9. A method as claimed in claim 8, wherein the desired solid support is used for solid phase synthesis of peptides, protected peptide fragments and small organic molecules.

10. A method as claimed in claim 9, wherein the resin of the formula 1 is used for solid phase synthesis of peptides through Boc chemistry protocol.

11. A method as claimed in claim 9, wherein the resin of the formula 1 is used for solid phase synthesis of peptides through Fmoc chemistry protocol.

12. A method as claimed in claim 9, wherein the resin of the formula 1 is used for solid phase synthesis of peptides through both Boc and Fmoc chemistry protocol separately or in combination.

13. A method as claimed in claim 9, wherein the resin of the formula 1 is used for the solid phase synthesis of heterocyclic small organic molecules.

14. A method as claimed in claim 9, wherein the resin of the formula 1 is used for the solid phase synthesis of small organic molecule for generation of combinatorial libraries.

15. A method as claimed in claim 9, wherein final products are cleaved from the desired solid support under mild alkaline conditions.

16. A method as claimed in claim 9, wherein final products are cleaved from the desired solid support using a mixture of 0.1–0.5 N aq. alkali and organic solvents selected from the group consisting of dioxane, tetrahydrofuran, methanol, ethanol, and dimethylformamide.

17. A method as claimed in claim 9, wherein the desired solid support has functional groups, wherein the desired solid support is used as scavenger resin and is treated with immobilized reagents after modification of the functional groups, wherein the functional groups are selected from the group comprising aldehyde, carboxylic, thiol, amino, and polyamino groups.

18. A method as claimed in claim 8, wherein reactions of step i are carried out in the presence of an organic solvent selected from the group consisting of methylene chloride, tetrahydrofuran, dimethylformamide, ether, petroleum ether, acetic acid, methanol in the presence of N,N'-dicyclohexylcarbodiimide, 1-hydroxybenzotriazole, and N-hydroxysuccinimide at a temperature ranging between 15° C. and 85° C.

19. A method as claimed in claim 8, wherein reactions of step i are performed using reagents selected from the group consisting of dicyclohexylcarbodiimide, mixed anhydride, active esters, benzotriazole-1-yl-oxy-tris-(dimethylamino) phosphonium hexafluorophosphate, benzotriazole-1-yl tetramethyluronium hexafluorophosphate, and 7-azabenzotriazole-l-yl tetramethyluronium hexafluorophosphate.

20. A method as claimed in claim 9, wherein acids are used for acidolytic cleavage of protecting groups, wherein the acids are selected from the group consisting of HBr:AcOH, HCl:Dioxane, formic acid, and trifluoroacetic acid.

21. A resin of the formula 1 as claimed in claim 1, wherein the resin of the formula 1 is stable at an ambient temperature for several months without any special storage conditions.

22. A resin of the formula 1 as claimed in claim 1, wherein the resin of the formula 1 is obtained from cheap and readily available raw materials.

23. A resin of the formula 1 as claimed in claim 1, wherein the resin of the formula 1 forms a solid support, and wherein a functionalized linker molecule is covalently attached to the solid support.

24. A method as claimed in claim 8, wherein amino acids that are prone to oxidation at C terminus can be used for synthesis of a peptide chain.

25. A method as claimed in claim 13, wherein the heterocyclic small organic molecules comprise thiazolidine derivatives.

* * * * *